(12) United States Patent
Neef

(10) Patent No.: US 8,591,810 B2
(45) Date of Patent: Nov. 26, 2013

(54) APPARATUS FOR HANDLING SPECIMEN SLIDES

(75) Inventor: Bernhard Neef, Nussloch (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 251 days.

(21) Appl. No.: 13/302,434

(22) Filed: Nov. 22, 2011

(65) Prior Publication Data

US 2012/0134893 A1 May 31, 2012

(30) Foreign Application Priority Data

Nov. 26, 2010 (DE) .......................... 10 2010 060 824

(51) Int. Cl.
*G01N 21/00* (2006.01)
(52) U.S. Cl.
USPC ............... 422/63; 422/50; 422/500; 422/501; 422/502; 422/536; 422/537; 422/64; 422/67; 436/180
(58) Field of Classification Search
USPC ............... 422/50, 500–502, 536–537, 64, 67; 436/180
See application file for complete search history.

(56) References Cited

U.S. PATENT DOCUMENTS

| 5,601,650 A | 2/1997 | Goldbecker et al. |
| 2003/0049172 A1 | 3/2003 | Thiem |
| 2004/0002163 A1 | 1/2004 | Reinhardt et al. |
| 2006/0231023 A1 | 10/2006 | Angros |
| 2007/0172911 A1 | 7/2007 | Farrell et al. |
| 2009/0110597 A1 | 4/2009 | Ljungmann et al. |

FOREIGN PATENT DOCUMENTS

| DE | 4117833 | 12/1992 |
| DE | 10144989 | 5/2003 |
| EP | 1717571 | 11/2006 |

*Primary Examiner* — Jyoti Nagpaul
(74) *Attorney, Agent, or Firm* — Hodgson Russ LLP

(57) ABSTRACT

An apparatus (10, 60, 70, 100, 110, 120) for handling specimen slides (21) encompasses a coverslipping module (14) for coverslipping thin sections arranged on the specimen slides (21), the coverslipping module (14) applying first a mounting medium and then a coverslipping means onto the specimen slides (21). The apparatus (10, 60, 70, 100, 110, 120) further has an output unit (18) for outputting the specimen slides (21), which unit encompasses a drying unit (32) for at least partial extraction of at least one solvent from the applied mounting medium of the specimen slides (21) arranged in the output unit (18).

20 Claims, 11 Drawing Sheets

APPARATUS FOR HANDLING SPECIMEN SLIDES

CROSS REFERENCE TO RELATED APPLICATIONS

This application claims priority of German patent application number 10 2010 060 824.6 filed Nov. 26, 2010, the entire disclosure of which is incorporated by reference herein.

FIELD OF THE INVENTION

The present invention relates to an apparatus for handling specimen slides that encompasses at least one coverslipping module for coverslipping thin sections arranged on the specimen slides.

BACKGROUND OF THE INVENTION

In histology, thin sections generated from tissue samples are mounted onto specimen slides. The thin sections mounted onto the specimen slides are then usually treated, for example stained and/or dewatered. The thin section is then covered with a coverslip in order to protect the thin sections. Prior to mounting of the coverslip, a mounting medium, by way of which the coverslip adheres to the specimen slide, is first applied. The coverslipped specimen slides are then delivered to a microscope.

A problem with known apparatuses for coverslipping thin sections arranged on specimen slides is that the coverslipped specimen slides must be handled very carefully, since upon removal of the specimen slides from the coverslipping module, the mounting medium has not yet dried and the coverslip can therefore slip off if the specimen slides are not held horizontally. The thin section can thereby be damaged. It is likewise possible for the coverslip, as a result of slippage, to protrude laterally beyond the specimen slide, so that a person handling the specimen slide can easily cut him- or herself thereon. This is problematic in particular when handling contaminated thin sections, since the operator is thus exposed to a risk of infection.

The document US 2009/0110597 A1 discloses an apparatus for handling specimen slides that encompasses a coverslipping module, a drying unit, and an output unit for outputting the coverslipped and dried specimen slides. Here the specimen slides are dried while they are being individually transported through the drying unit to the output unit, and are deposited individually in the output unit.

Further apparatuses and methods for coverslipping specimen slides are known from the documents US 2007/0172911 A1 and US 2006/0231023 A1.

The documents DE 101 44 989 A1 and DE 41 17 833 A1 describe stainers, for staining tissue samples arranged on specimen slides, that encompass a drawer for delivering and/or removing the specimen slides.

SUMMARY OF THE INVENTION

It is an object of the invention to describe an apparatus for handling specimen slides that is of compact configuration and with which thin sections arranged on the specimen slides can be coverslipped in simple fashion in such a way that the coverslipped specimen slides can easily be handled.

This object is achieved by an apparatus having the features described herein. Advantageous embodiments of the invention are indicated in the present specification.

The result of providing a drying unit for extracting solvent from the mounting medium applied onto the specimen slides is that the mounting medium dries quickly, and the coverslipping means thus adheres firmly to the specimen slide. The specimen slide can thus already be removed shortly after coverslipping, such that the coverslipping means cannot slip off even if the specimen slide is held askew. In particular, relatively rapid evaporation of the solvent is achieved by the drying unit. The fact that the drying unit is arranged in such a way that it dries the specimen slides arranged in the output unit yields a particularly compact configuration for the apparatus. In particular, it is possible to dispense with a separate drying unit in which the specimen slides are temporarily stored before being transported, after drying, to the output unit. The number of transport operations required for the specimen slides within the apparatus is thus also reduced.

Glass coverslips are used, in particular, as coverslipping means. The solvent encompasses, in particular, xylene, toluene, and/or water.

Extraction of solvent from the applied mounting medium is preferably achieved by delivering an air flow to the specimen slides through an air delivery unit of the drying unit. This air drying results in low-stress drying of the mounting medium, so that the thin sections mounted onto the specimen slides are not damaged. In particular, this ensures that a temperature at which the thin sections might be damaged is not reached by the thin sections during drying. In an alternative embodiment of the invention, a radiative heating unit with which the specimen slides can be irradiated with heat and thus dried can also be provided additionally or alternatively to the air delivery unit.

The apparatus encompasses in particular a transport unit with which the coverslipped specimen slides can be transported from the coverslipping module to the output unit. Automatic transportation of the coverslipped specimen slides from the coverslipping module to the output unit is thus provided, so that manual intervention can be dispensed with and there is assurance that as a result of transport using the transport unit, the horizontal position of the specimen slides is maintained during transport, and slippage of the coverslips is avoided. The result of integrating the drying unit into the output unit is that, as compared with the provision of a separate drying unit, the transport unit can be of simpler and more compact construction since it needs to be capable of traversing fewer different transport paths.

The specimen slides are received during transport, in particular, in one or more racks, so there is no need to transport each specimen slide individually. The result thereby achieved is that more specimen slides can be transported per unit of time. In addition, the handling of racks is simpler than the handling of individual specimen slides, in particular when the mounting medium is not yet dry. The specimen slides with the thin sections mounted onto them are introduced, preferably also in racks, into the apparatus via an input tray, and transported in the rack to the coverslipping module. After coverslipping, the coverslipped specimen slides are transported back into the rack before the latter is transported by the transport unit to the output unit. After drying of the mounting medium, the racks are removable in mechanized and/or manual fashion.

In an alternative embodiment of the invention, the specimen slides can also be transported individually from the coverslipping module to the output unit, and received individually in the output unit. In addition, it is alternatively possible for the specimen slides to be transported individually from the input unit to the coverslipping module. It is likewise possible for one portion of the above-described transport operations to occur inside racks, and for the specimen slides to be transported individually during another portion of the above-described transport operations.

The output unit preferably encompasses an output drawer in which the specimen slides to be outputted are stored, individually and/or received in racks, during drying with the aid of the drying unit. In a retracted state the output drawer is arranged inside a housing of the apparatus, whereas in an extended state the output drawer is arranged, for removal of the specimen slides to be outputted, at least partly outside the housing of the apparatus. The specimen slides received in the output drawer can thus easily be removed when the drawer is extended. Removal of the specimen slides or the racks from the extended output drawer can occur manually and/or automatically.

The apparatus encompasses in particular a drive unit with which the output drawer is displaceable from the retracted state into the extended state and/or from the extended state into the retracted state. This on the one hand results in convenient retraction and extension of the output drawer, and on the other hand ensures that the output drawer is extended and retracted carefully, so that the specimen slides that are received are not damaged. The drive unit encompasses, in particular, an electric motor.

In an alternative embodiment of the invention, the output drawer can, additionally or alternatively, also be manually displaceable from the retracted state into the extended state and/or from the extended state into the retracted state. It is thus possible to dispense with a drive unit, resulting in a simpler, more economical configuration of the apparatus.

Displacement of the output drawer from the retracted state into the extended state also terminates, or at least decreases, the action of the drying unit on the specimen slides received in the output drawer. The duration of action, and thus the degree of drying, can thus easily be controlled by a displacement of the output drawer from the retracted into the extended state. The drying unit is, in particular, operated continuously, and the duration of action and degree of drying are controlled by retracting and extending the output drawer mechanically or manually.

In a preferred embodiment of the invention, the output unit encompasses a housing that has a first opening for delivering racks or specimen slides with the aid of the delivery unit, and a second opening through which the output drawer is displaceable. The specimen slides or racks can be delivered in simple fashion to the output unit through the first opening. The racks or specimen slides can easily be removed from the apparatus through the second opening. Simple handling of the specimen slides or racks is thus achieved.

The housing of the output unit can be constituted, in at least a sub-region, by the housing of the apparatus. In particular, the housing of the output unit is constituted, in the sub-region in which the output drawer is arranged, by the housing of the apparatus. The output drawer encompasses, in particular, a front wall that, when the output drawer is retracted, forms part of the housing of the apparatus and part of the housing of the output unit.

The front wall of the output drawer closes off the second opening in particular when the output drawer is arranged in the retracted state. This prevents the air flow from escaping from the apparatus, in particular from the output unit.

The output unit is closed off by the output unit with respect to the rest of the apparatus, so that the air flow that is guided along past the specimen slides to be dried cannot escape into the rest of the apparatus. Simple, controlled drying of the coverslipping media of the specimen slides received in the output unit is thereby achieved. In addition, the housing protects the specimen slides received in it.

The first opening is preferably closable and openable, so that no air flow can escape when the housing is closed. Closure of the first opening occurs, in particular, by way of a sliding door, so that little installation space is required, especially compared with a swing-out door. A compact, space-saving configuration of the apparatus is thereby achieved.

In a preferred embodiment of the invention, at least one sub-region of the housing of the output unit is insulated with the aid of an insulating medium, so that a thermal separation is achieved between the interior space surrounded by the housing of the output unit and the remainder of the apparatus. It is particularly advantageous if the entire housing of the output unit is insulated. Additionally or alternatively, the sliding door can also be insulated. Insulation reduces heat losses, so that less energy has to be supplied in order to heat the air flow to a preset temperature.

In this context, the racks are receivable in the output unit in such a way that the specimen slides arranged in the received rack are arranged horizontally, thereby avoiding slippage of the covering means while the mounting medium has not yet dried.

The drying unit can furthermore encompass an air discharge unit for discharging air from the specimen slides. The air flow delivered by the air delivery unit is thereby discharged, thus achieving a continuous flow of air around the specimen slides.

The air discharge unit is, in particular, embodied in such a way that it encompasses a fan with which the air to be discharged is aspirated out of the output unit. The air delivery unit also preferably encompasses a fan with which the air to be delivered is blown toward the racks through a delivery conduit.

In a particularly preferred embodiment of the invention, the air delivery unit delivers to the specimen slides an air flow having a preset temperature. The preset temperature has, in particular, a value between 40° C. and 70° C., preferably between 40° C. and 50° C.

The result of delivering a temperature-controlled air flow is that the heated air can receive more solvent than colder air, in particular air at room temperature, so that the coverslipping media of the specimen slides arranged in the output unit dry more quickly, and the time that the specimen slides must spend in the output unit is reduced. Delivery of an air flow having a temperature between 40° and 50° ensures on the one hand that rapid drying occurs, and on the other hand that damage to the thin sections due to excessively high temperature is avoided.

To heat the air flow, the drying unit encompasses, in particular, a heating element that heats the air flow before it is delivered to the racks. The heating element is arranged, in particular, at an end of the air delivery unit remote from the received racks, so that the greatest possible spacing between the heating element and the racks is achieved. This avoids the possibility that the thin sections mounted onto the specimen slides arranged in the drying unit might be damaged by excessively high temperatures. A particular result of this is that the thin sections are not directly exposed to radiated heat from the heating element.

It is further advantageous if a sensor for ascertaining the actual temperature of the air flow is provided. A control unit compares the actual temperature with a preset temperature, and applies control to the heating element as a function of the result of that comparison so that the delivered air flow has the target temperature. This also ensures that the preset target temperature is in fact reached. Rapid and sufficient drying of the specimen slides is thus achieved, and damage to the thin sections due to excessively high temperatures is avoided. Control is applied to the heating element, in particular, in the form of closed-loop control.

The air delivery unit is embodied in particular in such a way that the air flow has a flow velocity of between 0.5 m/s and 1.5 m/s, and/or a volumetric flow rate of between 4 m$^3$/h and 5 m$^3$/h. In this case, drying of the mounting media sufficient to prevent the coverslips from slipping is achieved within three minutes at an air flow temperature between 50° and 60°, so that the racks received in the output unit can be removed after only three minutes. A higher throughput is thereby ensured.

In a particularly preferred embodiment of the invention, the drying unit encompasses at least one sensor with which an actual flow velocity and/or an actual volumetric flow rate are detectable. The control unit compares the ascertained actual flow velocity and/or the ascertained actual volumetric flow rate with a preset target flow velocity or with a preset target volumetric flow rate, respectively, and applies control to the air delivery unit in such a way that an air flow having the preset target flow velocity and/or the preset target volumetric flow rate is guided to the specimen slides. Control is applied, in particular, in the form of closed-loop control.

It is furthermore advantageous if a filter, in particular an activated carbon filter, is provided for filtering the air to be delivered. This prevents any modifications, as a result of dirty and/or contaminated air, to the thin sections mounted onto the specimen slides being dried, with the consequence that the subsequent result in the context of microscopy of the thin sections might be incorrect. Additionally or alternatively, a further filter, in particular an activated carbon filter, can be provided in order to filter the discharged air. The result of this is that the air emitted to the environment is not contaminated. This is necessary in particular when the thin sections have such contamination.

It is additionally advantageous if a bottom element of the output drawer, on which element the racks or specimen slides are supported, comprises at least one opening, preferably multiple openings, through which the air delivery unit delivers the air flow. The result achieved thereby is that the heated air can rise from bottom to top in accordance with its natural behavior, so that no (or only a few) means for guiding the air are necessary. Delivery and discharge of the air flow is accomplished, in particular in such a way that the air flow passes in vortex-like fashion through the interstices embodied between two specimen slides arranged adjacent to one another in the rack, so that good drying is achieved within a short time.

In an alternative embodiment of the invention, a respective slit nozzle for delivering the air flow can be provided on two oppositely located side walls of the drying chamber. The slit nozzles are arranged in such a way that their longitudinal direction extends vertically. The slit nozzles moreover are preferably embodied to be longer than the racks, thereby achieving reliable flow around even the outermost specimen slides in the rack. Aspiration of the air to be discharged occurs in this case in particular through at least one opening of the bottom element. Alternatively, the air to be discharged can also be aspirated above the racks.

In an alternative embodiment, the output drawer can also have no side wall. In this case the slit nozzles are arranged on two oppositely located side walls of the housing of the output unit and/or on separate oppositely located side walls, provided therefor, inside the housing of the output unit.

The air delivery unit has, in particular, at least one air delivery conduit for delivering the air flow, and the air discharge unit has at least one air discharge conduit for discharging the air that is to be discharged. In a preferred embodiment of the invention, the air delivery conduit and the air discharge conduit are embodied in such a way that they extend directly next to one another at least in a sub-region, and in particular are embodied integrally in a sub-region of the respective delimiting walls of the air discharge conduit and the air delivery conduit. A compact, space-saving configuration is thereby achieved.

BRIEF DESCRIPTION OF THE DRAWINGS

Further features and advantages of the invention are evident from the description below, which explains the invention further on the basis of exemplifying embodiments in conjunction with the attached Figures, in which.

DETAILED DESCRIPTION OF THE INVENTION

Figure 1:
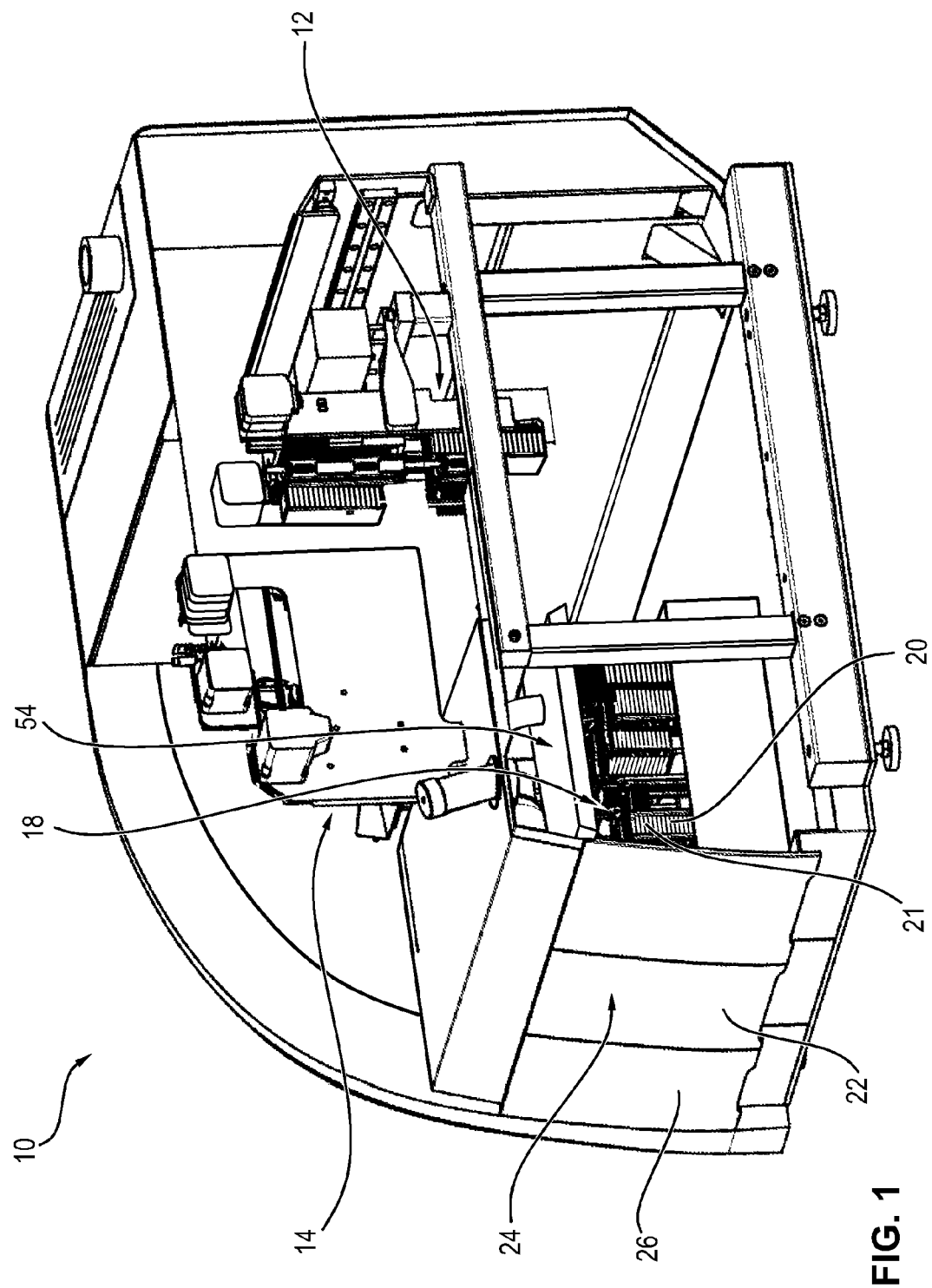
FIG. 1 is a schematic perspective depiction of a coverslipper in accordance with a first embodiment of the invention, with a retracted output drawer.

FIG. 1 is a schematic perspective depiction of an apparatus for handling specimen slides, embodied as a coverslipper 10. Coverslipper 10 encompasses an input unit 16 (not visible in FIG. 1) with which racks, having specimen slides received in them, can be delivered to coverslipper 10. A rack arranged in an output unit 18 is labeled, by way of example, with the reference character 20, and a specimen slide, by way of example, with the number 21. Delivery can occur both manually and automatically with the aid of a delivery unit. Both a standalone mode, in which coverslipper 10 is not connected to further apparatuses for handling specimen slides, and a workstation mode, are thus possible. In workstation mode, coverslipper 10 is arranged, in particular, adjacently to a stainer; once the thin sections arranged on specimen slides 21 have been stained, the latter, received in racks 20, are automatically transferred from the stainer to coverslipper 10.

Coverslipper 10 further has a transport unit 12 with which racks 20, inputted via the input unit, can be transported to a coverslipping module 14. In coverslipping module 14, specimen slides 21 are removed individually from rack 20. First a mounting medium is applied onto specimen slide 21 that has been removed, and then a coverslipping means, in particular a glass coverslip, is mounted onto the mounting medium. The thin section is thereby protected by the coverslip, and a clear presentation is guaranteed upon microscopy of the thin section. Once the thin section on specimen slide 21 has been coverslipped, the specimen slide is transported back into rack 20 and the next specimen slide 21 is removed for coverslipping.

Once all the specimen slides 21 of rack 20 have been coverslipped, transport unit 12 transports rack 20 into output unit 18. The latter is embodied in such a way that a plurality of racks 20 are receivable therein. Racks 20 can be removed manually and/or automatically from output unit 18 before then being delivered to a microscope for microscopy.

Output unit 18 encompasses an output drawer 22 in which racks 20 are received. In a retracted state shown in FIG. 1, output drawer 22 is arranged in such a way that racks 20 are arranged in the interior of coverslipper 10. In the retracted state, output drawer 22 is arranged, in particular, in such a way that a front wall 24 of output drawer 22 is arranged in one plane with a part of housing 26 of coverslipper 10, so that housing 26 and front wall 24 close off the interior space of coverslipper 10, preferably in air-tight fashion. Escape of air from the interior space of coverslipper 10 into the environment is thus prevented when output drawer 22 is in the retracted state.

Figure 2:
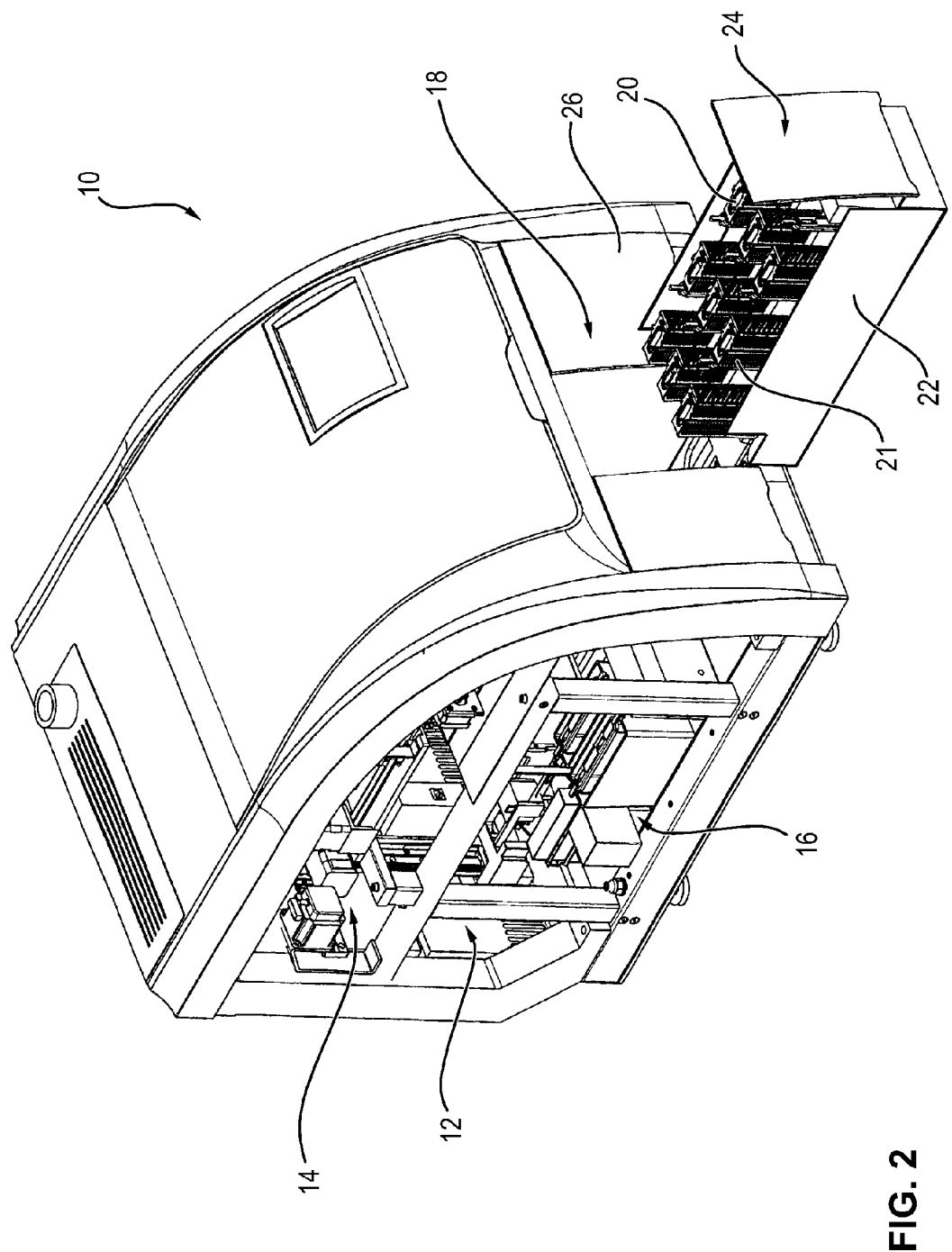
FIG. 2 is a schematic perspective depiction of the coverslipper of FIG. 1, with the output drawer extended.

With output drawer 22 in the extended state shown in FIG. 2, the drawer is arranged at least partly outside the interior space, surrounded by housing 26, of coverslipper 10. Output drawer 22 is in particular, in the extended state, extended sufficiently far out of coverslipper 10 that access to all the racks 20 received in output drawer 22 is possible.

Figure 3:
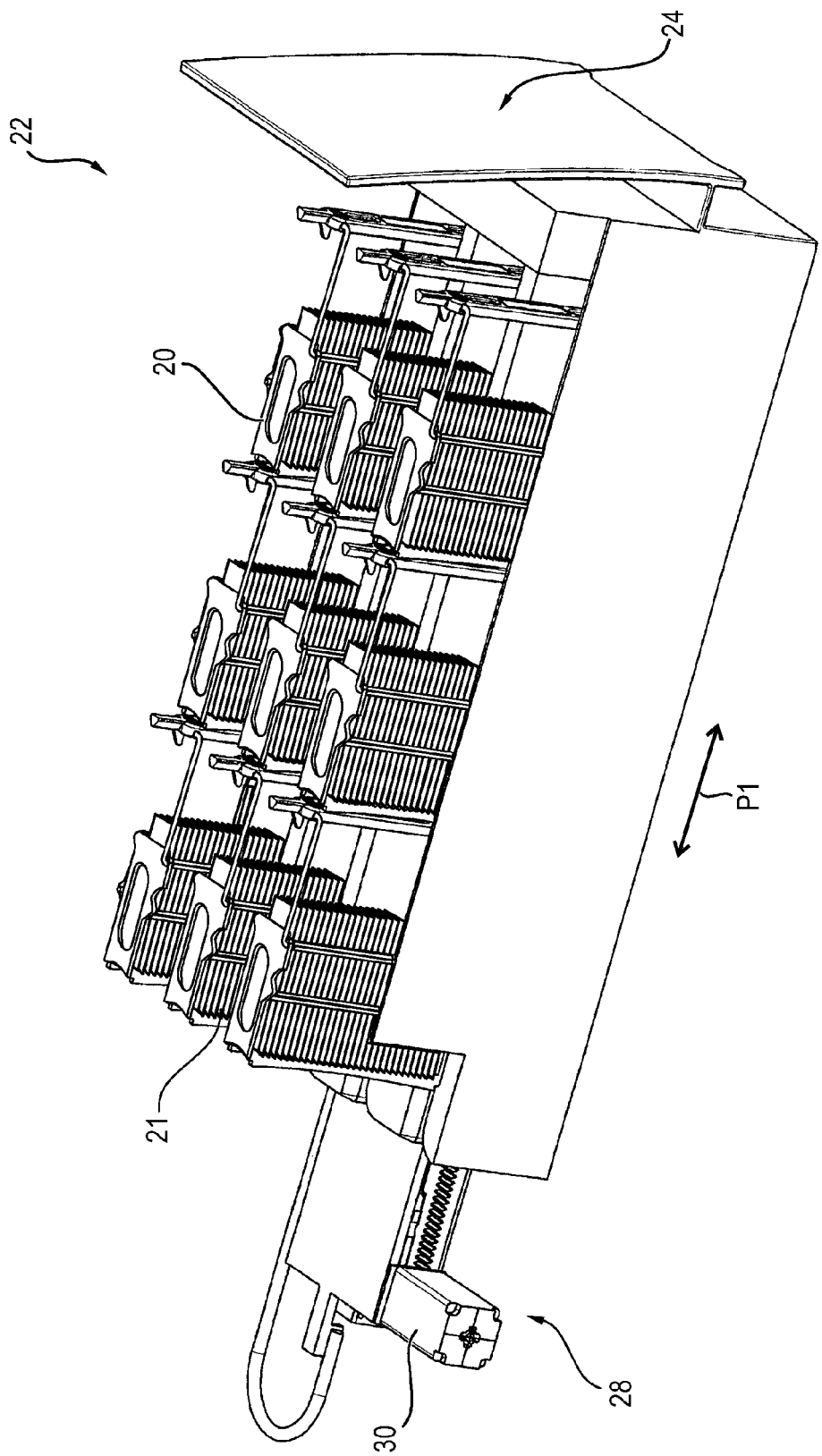
FIG. 3 is a schematic perspective depiction of the output drawer.

FIG. 3 is a schematic perspective depiction of output drawer 22 according to FIGS. 1 and 2. Racks 20 are received in such a way that three racks 20 are received one behind another when viewed respectively in displacement direction P1. In addition, three racks 20 are received next to one another in each case. In the first exemplifying embodiment a total of nine racks 20 are thus receivable simultaneously in output drawer 22. In an alternative embodiment of the invention, more than nine racks 20 or fewer than nine racks 20 can also be receivable in output drawer 22. In addition, the arrangement of racks 20 in output drawer 22 can differ from the arrangement shown in FIGS. 1 to 3.

Coverslipper 10 encompasses a drive unit 28 with which output drawer 22 can be displaced from the retracted into the extended state and vice versa. Drive unit 28 comprises, in particular, an electric motor 30.

In an alternative embodiment of the invention, output drawer 22 can also be displaced manually from the extended into the retracted state and vice versa. It is also alternatively possible for coverslipper 10 to be embodied in such a way that output drawer 22 is displaceable both with the aid of drive unit 28 and manually.

Figure 4:
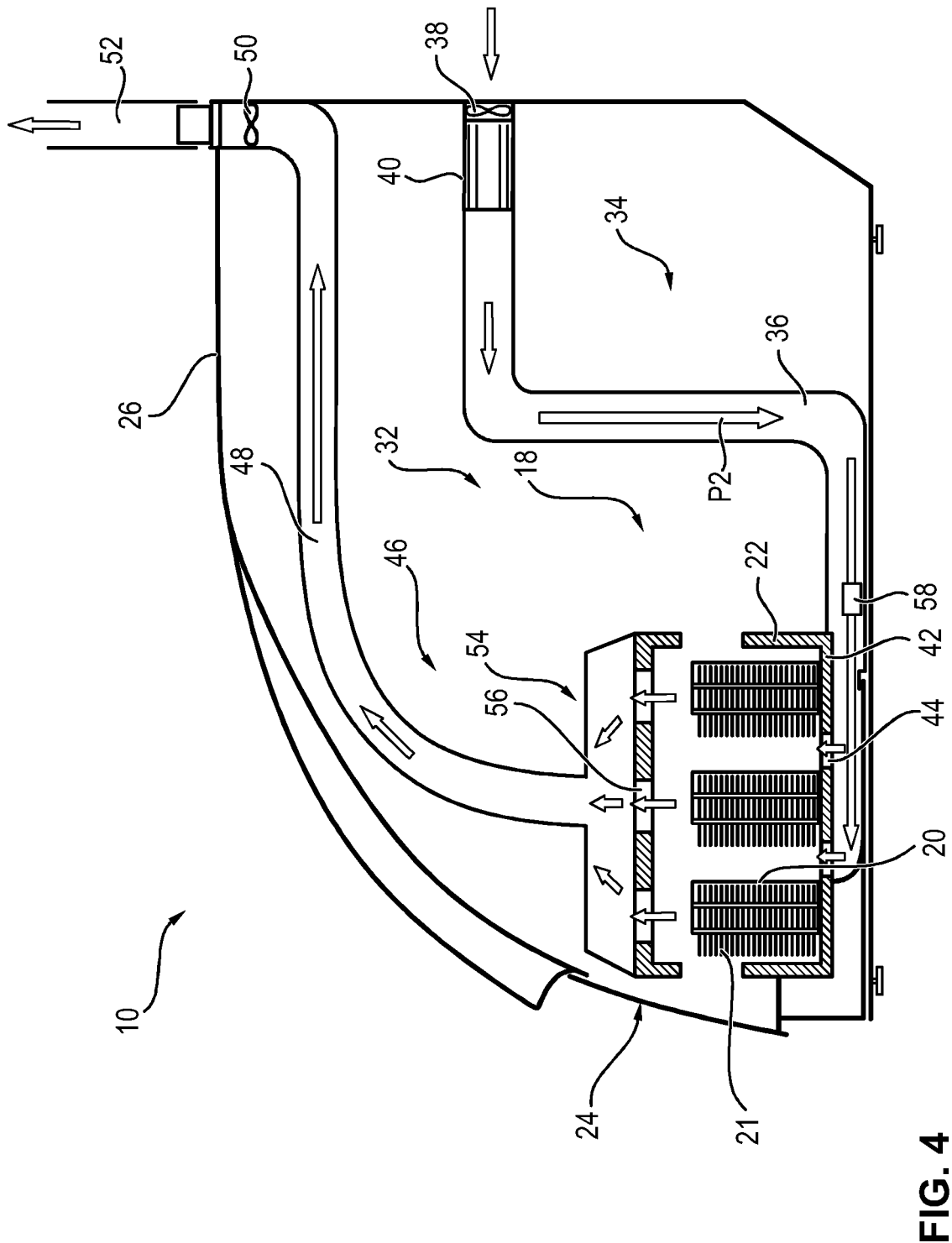
FIG. 4 is a schematic, highly simplified depiction of the coverslipper according to FIGS. 1 and 2 with the output drawer retracted.
Figure 5:
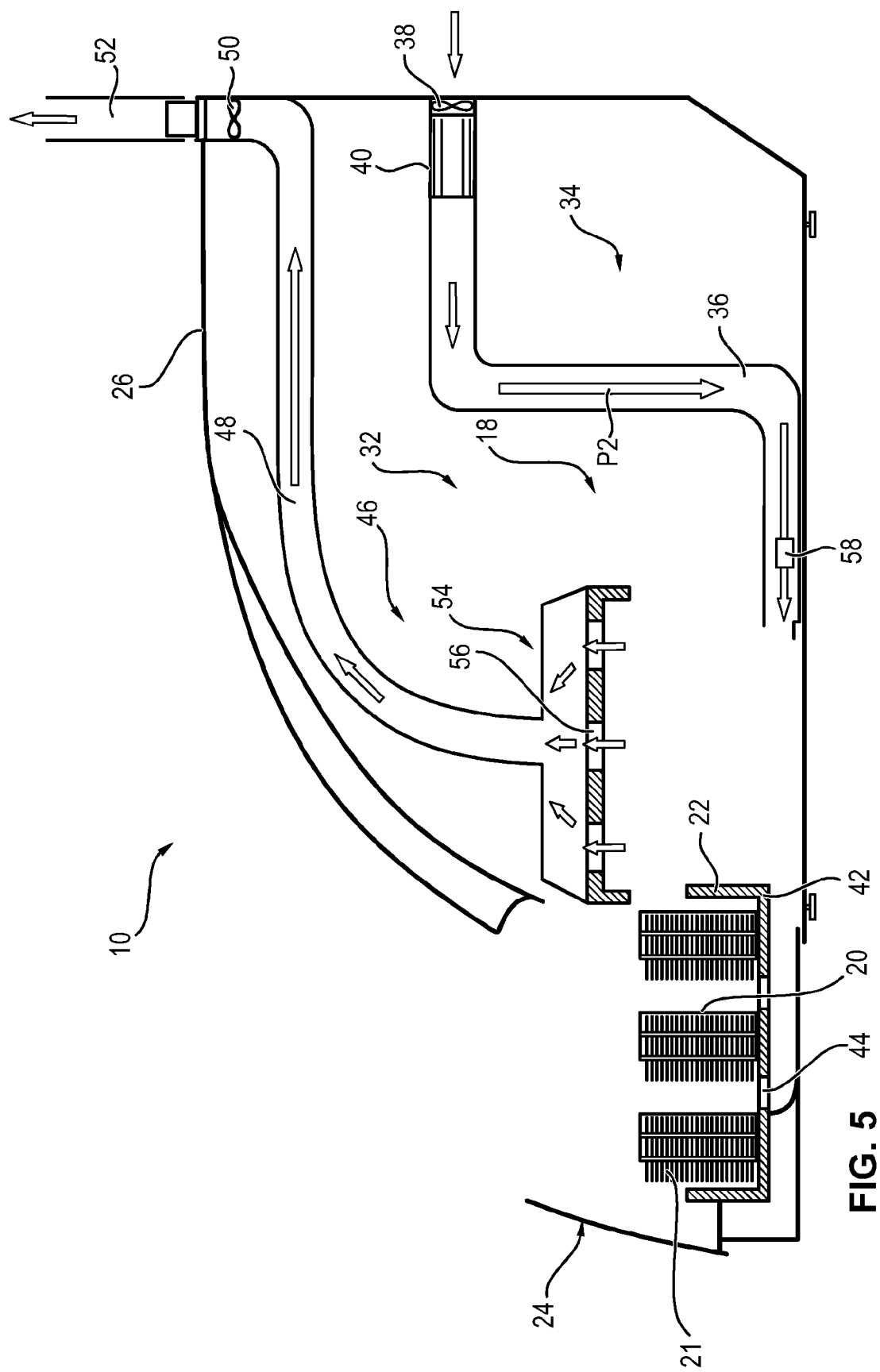
FIG. 5 is a schematic, highly simplified depiction of the coverslipper according to FIGS. 1, 2, and 4, with the output drawer extended.

A schematic, highly simplified depiction of coverslipper 10 according to FIGS. 1 and 2 is shown in FIG. 4 with output drawer 22 retracted, and in FIG. 5 with output drawer 22 extended. Output unit 18 encompasses a drying unit 32 with which specimen slides 21 received in racks 20, which are received in output drawer 22, are dried. With drying unit 32, at least one solvent applied by way of the mounting medium is at least partly extracted from the mounting medium, so that the mounting medium dries and the coverslip adheres to specimen slide 21. Drying unit 32, in particular, produces comparatively rapid evaporation of the solvent so that specimen slides 21 dry in a relatively short time as compared with a coverslipper that does not possess a drying unit, so that specimen slides 21 can be removed with no slippage of the coverslips.

Drying unit 32 is embodied in such a way that specimen slides 21 are dried while they are received in output drawer 22 and thus in output unit 18. The result is that a compact space-saving configuration is achieved, as compared with a separate drying unit 32 in which specimen slides 21 are temporarily stored after coverslipping before then being transported further, after drying, into output unit 18. The duration of action of drying unit 32, and thus the degree of solvent extraction, can be regulated in particular by way of the length of time spent by specimen slides 21 inside output unit 18.

Drying unit 32 encompasses an air delivery unit 34 through which an air flow is guided to racks 20 received in output drawer 22. The air flow is indicated by the block arrow, one of which is designated by way of example by the reference character P2. Air delivery unit 34 has an air delivery conduit 36, a fan 38, and a heating element 40 for heating the air flow that is to be delivered. Heating element 40 heats the air flow, in particular, in such a way the latter has a temperature between 50 and 60° C. The drying of the mounting media of specimen slide 21 achieved within three minutes is thus sufficient that the coverslips can no longer slip off even if specimen slides 21 are not held horizontally. A high throughput of specimen slides 21 is thereby obtained.

Air delivery unit 34 is furthermore embodied, in particular, in such a way that an air flow having a flow velocity between 0.5 m/s and 1.5 m/s, and a volumetric flow rate between 4 $m^3/h$ and 5 $m^3/h$, is generated by it.

A bottom element 42 of output drawer 22 encompasses multiple openings, one of which is designated by way of example with the reference character 44. Through these openings 44, air from air delivery unit 34 is delivered from below to specimen slides 21 so that the heated air rises upward in accordance with its natural behavior, and in that context preferably flows around specimen slides 21 received in racks 20, so that the mounting media of specimen slides 21 dry in the shortest possible time.

Drying unit 32 furthermore has an air discharge unit 46 with which the cooled and solvent-containing air is discharged. Air discharge unit 46 encompasses in particular an air discharge conduit 48 and a fan 50, with which air is aspirated from racks 20 received in output drawer 22 and is delivered to a central exhaust disposal unit 52. Air discharge unit 46 encompasses an aspiration element 54, arranged above that region of output drawer 22 in which racks 20 are arranged, that comprises multiple openings 56 through which air is aspirated. Air discharge unit 46 on the one hand maintains a continuous air flow, and on the other hand prevents the formation inside coverslipper 10 of explosive mixtures and/or mixtures hazardous to health.

Also provided is a sensor 58 with which the actual temperature of the delivered air flow is ascertained. A control unit (not depicted) compares the actual temperature with a preset target temperature, and applies control to heating element 40 as a function of the result of that comparison. This ensures that the air flow in fact has at least approximately the preset target temperature. Damage to the samples as a result of excessively hot temperatures, but also insufficient drying resulting from an excessively cold air flow, are thus avoided. The temperature of the air flow is controlled, in particular, in the form of a closed control loop.

Heating element 40 is arranged, in particular, at the end of air delivery conduit 36 remote from output drawer 22, so that heating element 40 is arranged as far away as possible from specimen slides 21, so that no direct heat radiation from heating element 40 acts on specimen slides 21, and damage to the thin sections is thereby avoided.

Figure 6:
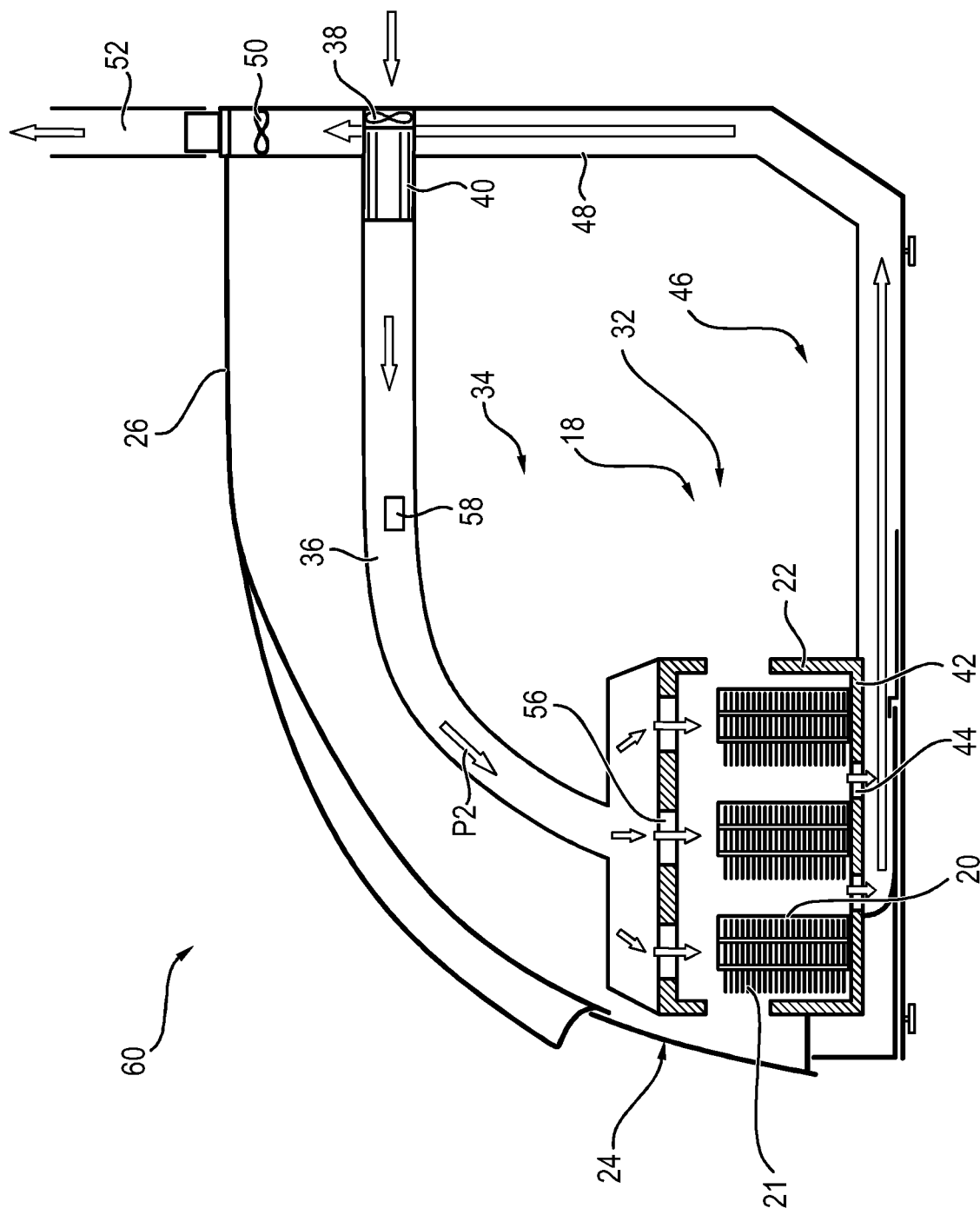
FIG. 6 is a schematic, highly simplified depiction of a coverslipper according to a second embodiment of the invention.

FIG. 6 is a schematic, highly simplified depiction of a coverslipper 60 according to a second embodiment of the invention. Output drawer 22 is depicted in FIG. 6 in the retracted state.

In contrast to the first exemplifying embodiment according to FIGS. 1 to 5, in the second exemplifying embodiment according to FIG. 6 the air delivery unit 34 delivers the air flow to racks 20 from above. Air discharge unit 46 aspirates air through openings 44 of bottom element 42 of output drawer 22, and delivers it to central exhaust disposal unit 52.

In an alternative embodiment of the invention, output unit 18 can also not encompass an output drawer 22. In this case output unit 18 encompasses an opening, closable via a closure element, in particular a panel and/or a door, through which racks 20 received in output unit 18 are manually and/or mechanically removable after drying. In this case removal of racks 20 requires access into the interior space of coverslipper 10, 60 delimited by housing 26 so that racks 20 can be transported out of the interior space.

Figure 7:
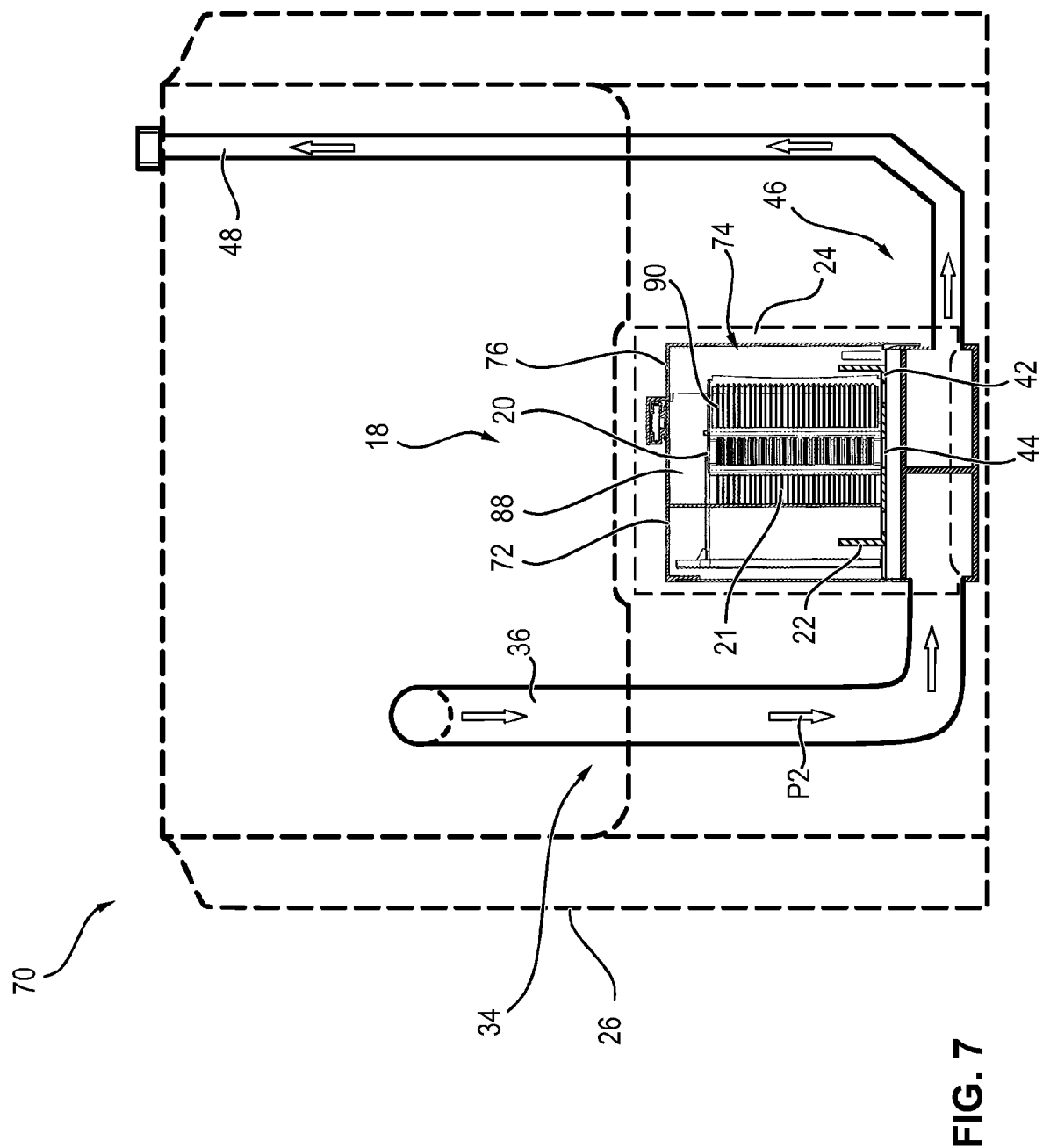
FIG. 7 is a schematic, highly simplified depiction of a coverslipper according to a third embodiment of the invention.

FIG. 7 is a schematic, highly simplified depiction of a coverslipper 70 according to a third embodiment of the invention. In this embodiment, output unit 18 encompasses a housing 72 by which an interior space 88 of output unit 18 is delimited. In the retracted state, racks 20 are arranged in interior space 88. Housing 72 is at least partly insulated, thereby achieving a thermal separation of interior space 88 with respect to the space surrounding output unit 18. The energy consumption required for drying the mounting media is thus reduced. In addition, housing 72 prevents the escape of solvent-containing air. Housing 72 moreover makes possible even more accurate guidance of the air flow through air delivery unit 34 and air discharge unit 46.

Housing 72 encompasses a first opening 74 through which racks 20 are delivered by transport unit 12 of output unit 18 and supported on output drawer 22. First opening 74 is closable with the aid of a sliding door 76, so that a closed housing 72 is achieved. The configuration of door 76 as a sliding door 76 results in a particularly compact and space-saving configuration.

Housing 72 furthermore encompasses a second opening (not visible in FIG. 7) through which output drawer 22 is displaceable between the retracted and the extended state. In the retracted state, front wall 24 closes off this second opening in particular, so that in the retracted state, interior space 88 through which the air flow passes is closed off, preferably in air-tight fashion, by housing 72, sliding door 76, and front wall 24. The delivery and discharge of air can occur in the third exemplifying embodiment analogously to the delivery and discharge described in connection with the first and the second exemplifying embodiment.

Figure 8:
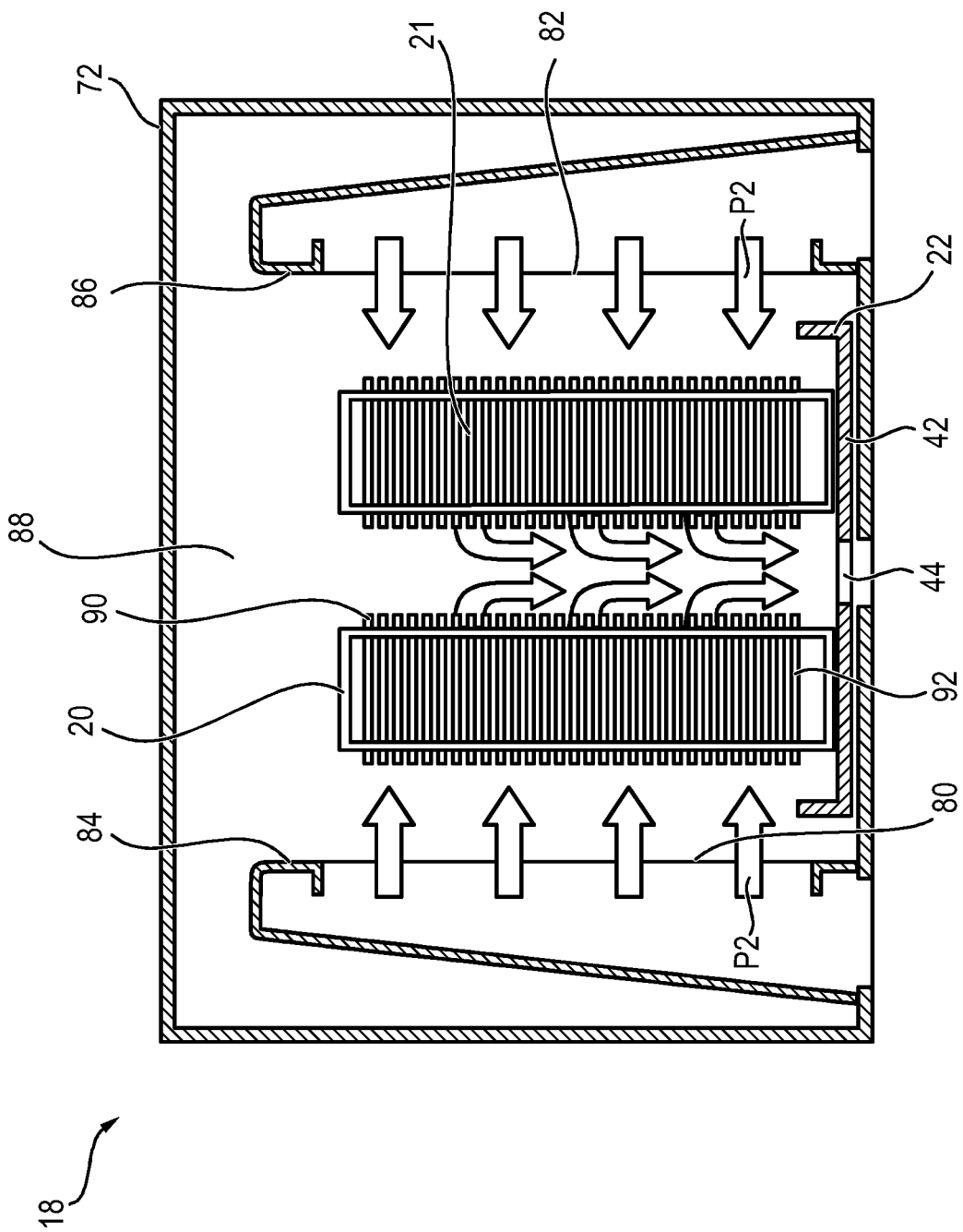
FIG. 8 is a schematic sectioned depiction of an output unit of a coverslipper according to a fourth embodiment of the invention.

FIG. 8 is a schematic sectioned depiction of an output unit 18 of a coverslipper in accordance with a fourth embodiment of the invention. In this fourth embodiment of the invention, output unit 18 encompasses two slit nozzles 80, 82, which are arranged on two oppositely located side walls 84, 86 and through which the air flow is delivered from air delivery unit 34 to interior space 88, delimited by housing 72, of output unit 18. Slit nozzles 80, 82 are arranged so that their longitudinal direction extends vertically. Slit nozzles 80, 82 are furthermore embodied so that they are at least as long as the spacing between the top outermost specimen slide 90 and the bottom outermost specimen slide 92. In a preferred embodiment of the invention, slit nozzles 80, 82 are embodied in such a way that they are a little longer than the spacing between outermost specimen slides 90, 92 in order to ensure a flow around even outermost specimen slides 90, 92.

The result obtained from slit nozzles 80, 82 is that the air flow is guided through specimen slides 21 arranged horizontally in racks 20 so that a sufficient flow of heated air is delivered around specimen slides 21. As the delivered air flows around racks 20, it cools and picks up solvent. After flowing through racks 20, the cooled air drops downward and is aspirated centeredly in the lower region, through opening 44 of bottom element 42 of output drawer 22, with the aid of air discharge unit 46.

Figure 9:
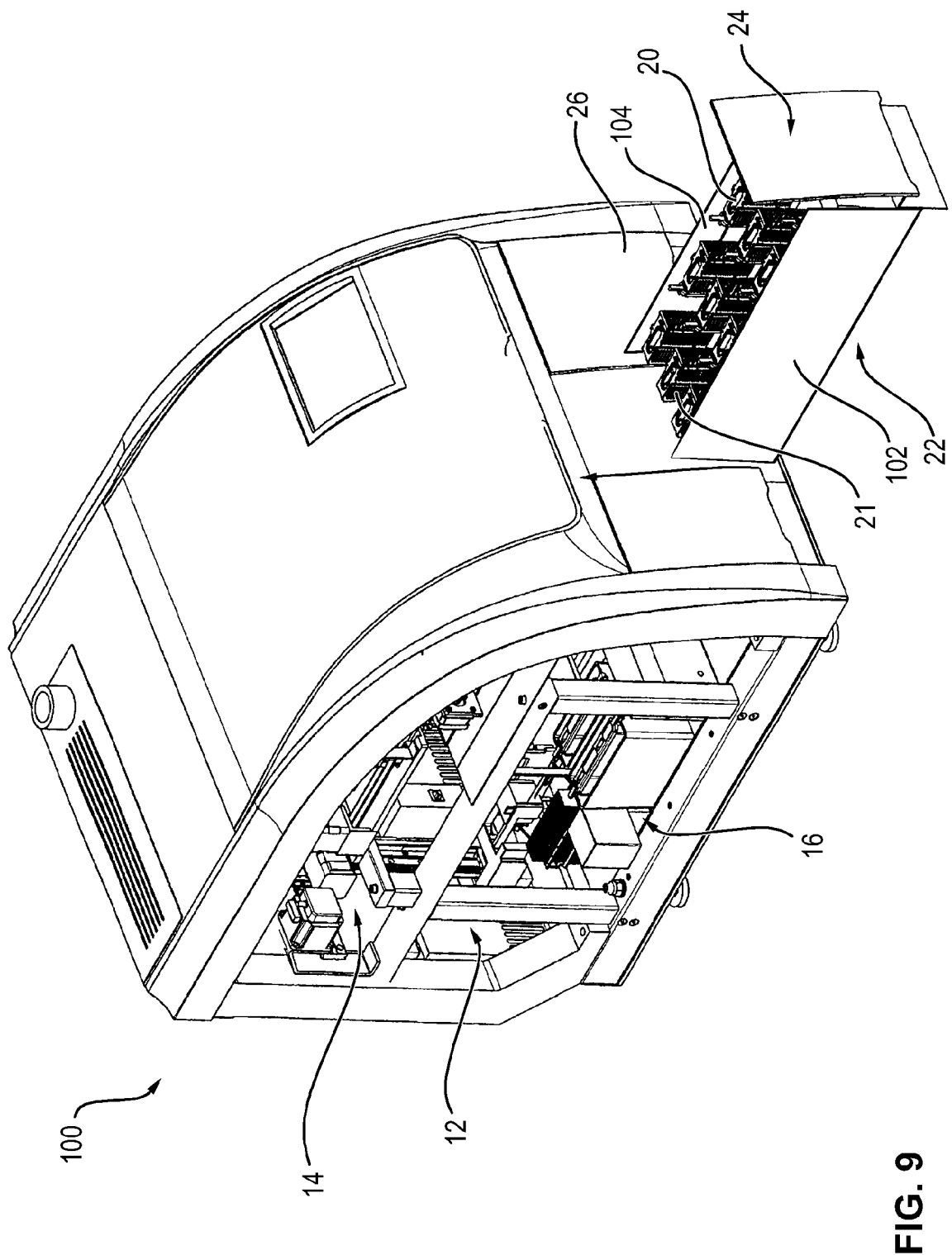
FIG. 9 is a schematic perspective depiction of a coverslipper according to a fifth embodiment of the invention.

FIG. 9 is a schematic perspective depiction of a coverslipper 100 according to a fifth embodiment of the invention. In this fifth embodiment of the invention, side walls 102, 104 of output drawer 22 are embodied to be at least as high as racks 20 received in output drawer 22. In the retracted state, side walls 102, 104 form the side walls of housing 72 of output unit 18, so that separate side walls are not needed. A simple, compact, and economical configuration is thereby achieved. In addition, the volume of interior space 88 is thereby reduced so that less energy is needed for heating.

Figure 10:
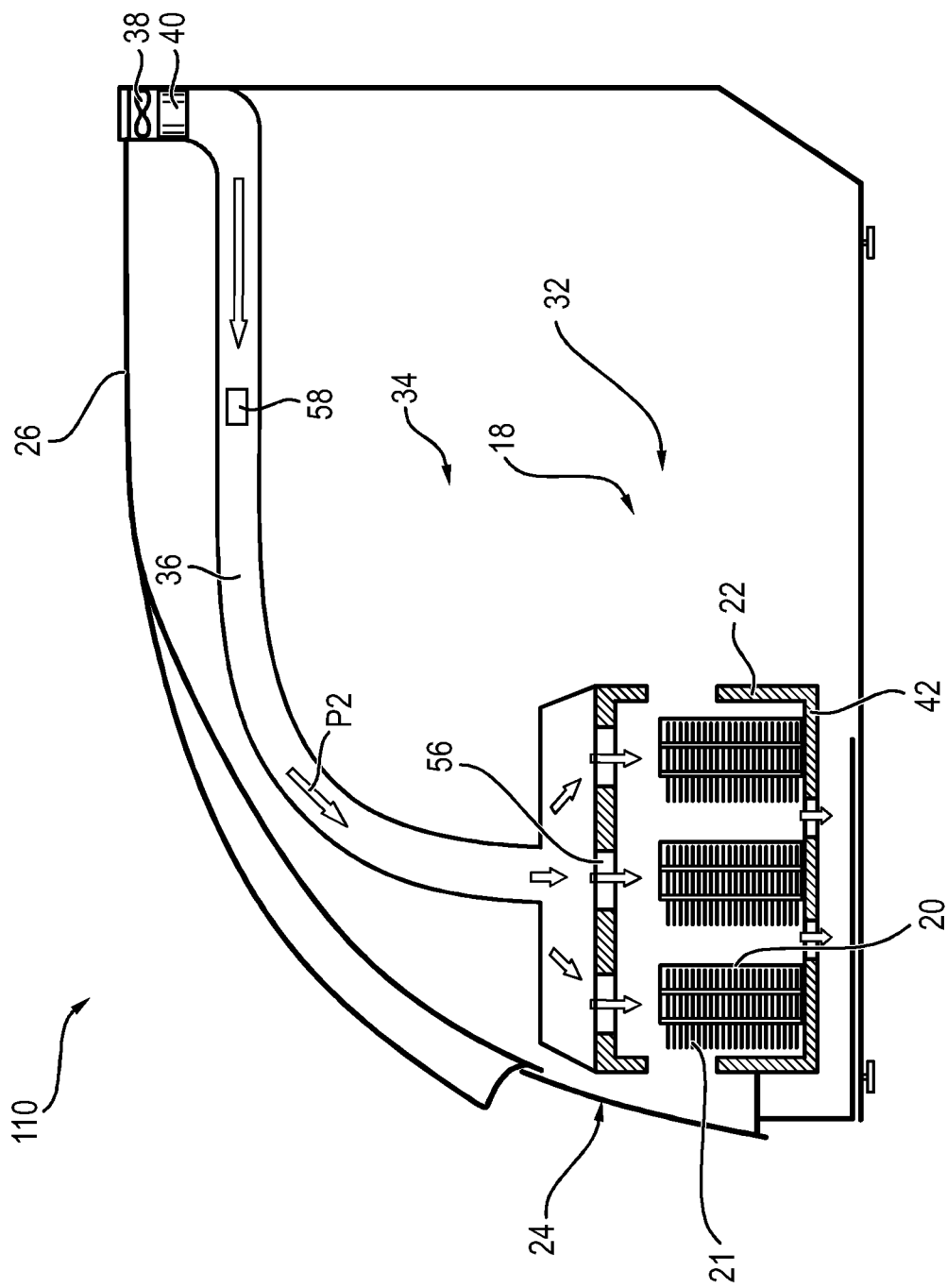
FIG. 10 is a schematic, highly simplified depiction of a coverslipper according to a sixth embodiment of the invention.

FIG. 10 is a schematic, highly simplified depiction of a coverslipper 110 according to a sixth embodiment of the invention. In this sixth embodiment, drying unit 32 encompasses only an air delivery unit 34 for delivering an air flow, but no air discharge unit 46 for controlled discharge of the cooled, solvent-containing air.

Figure 11:
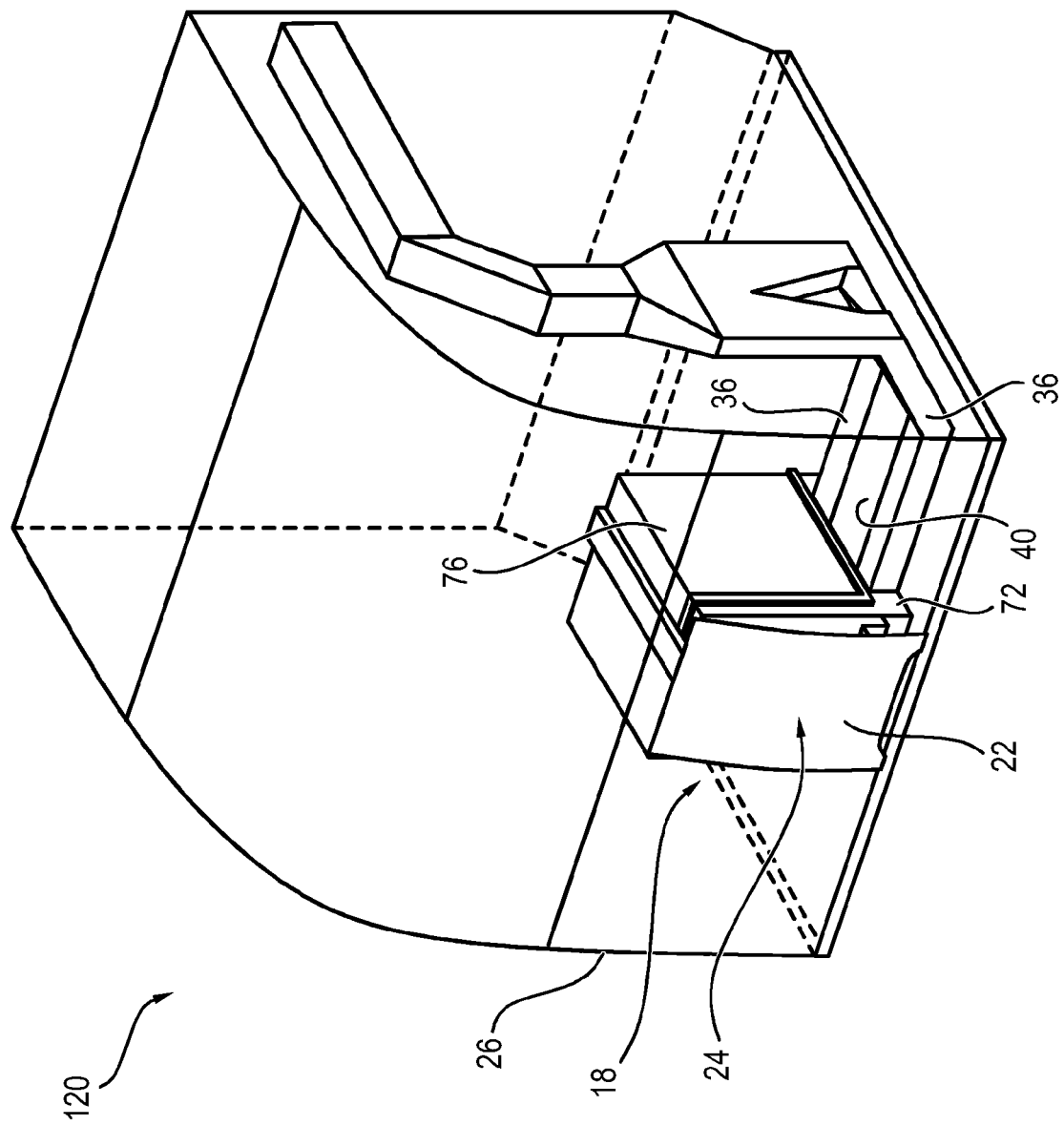
FIG. 11 is a schematic, highly simplified depiction of a coverslipper according to a seventh embodiment of the invention.

FIG. 11 is a schematic, highly simplified depiction of a coverslipper 120 according to a seventh embodiment of the invention. In accordance with a seventh embodiment, a subregion of air discharge conduit 48 is arranged between delivery conduit 36. A particularly compact configuration is thereby achieved.

The invention is not to be limited to the specific embodiments disclosed, and modifications and other embodiments are intended to be included within the scope of the invention.

LIST OF REFERENCE NUMERALS 10, 60, 70, 100, 110, 120 Coverslipper
12 Transport unit
14 Coverslipping module
16 Drying unit
18 Output unit
20 Rack
21 Specimen slide
22 Output drawer
24 Front wall
26 Housing
28 Drive unit
30 Electric motor
32 Drying unit
34 Air delivery unit
36 Air delivery conduit
38, 50 Fan
40 Heating element
42 Bottom element
44, 56 Opening
46 Air discharge unit
48 Air discharge conduit
52 Exhaust disposal unit
54 Aspiration element
58 Sensor
72 Housing
74 Opening
76 Sliding door
80, 82 Slit nozzle 84, 86 Side wall
88 Interior space
90, 92 Outermost specimen slide
102, 104 Side wall
P1 Displacement direction
P2 Air flow

What is claimed is:

1. An apparatus for handling specimen slides, comprising:
at least one coverslipping module (14) for coverslipping thin sections arranged on the specimen slides (21), the at least one coverslipping module (14) configured to apply a mounting medium onto the specimen slides (21) and then apply a coverslipping means onto each of the specimen slides (21);
an output unit (18) for outputting the coverslipped specimen slides (21), wherein the output unit (18) includes a drying unit (32) for at least partial extraction of at least one solvent from the applied mounting medium while the specimen slides (21) are arranged in the output unit (18); and
a transport unit (12) for transporting the coverslipped specimen slides (21) from the coverslipping module (14) to the drying unit (18), the transport unit (12) being configured to transport racks (20) carrying the coverslipped specimen slides to the output unit (18);
wherein the output unit (18) further includes an output drawer (22) arranged to receive and support the racks (20) carrying the coverslipped specimen slides (21).

2. The apparatus (10, 60, 70, 100, 110, 120) according to claim 1, wherein the drying unit (32) includes an air delivery unit (34) for delivering an air flow to the coverslipped specimen slides (21).

3. The apparatus (10, 60, 70, 100, 110, 120) according to claim 2, wherein the air delivery unit (34) includes a heating element (40) for warming the air flow delivered by the air delivery unit (34).

4. The apparatus (10, 60, 70, 100, 110, 120) according to claim 2, wherein the air delivery unit (34) is configured to deliver air flow having a preset temperature.

5. The apparatus (10, 60, 70, 100, 110, 120) according to claim 2, wherein the air delivery unit (34) is configured to deliver air flow having a flow velocity of between 0.5 m/s and 1.5 m/s.

6. The apparatus (10, 60, 70, 100, 110, 120) according to claim 2, wherein the air delivery unit (34) is configured to deliver air flow having a volumetric flow rate of between 4 m3/h and 5 m3/h.

7. The apparatus (10, 60, 70, 100, 110, 120) according to claim 2, wherein the air delivery unit (34) includes a filter for filtering the air flow to the coverslipped specimen slides (21).

8. The apparatus (10, 60, 70, 100, 110, 120) according to claim 1, further comprising a housing (26), wherein the output drawer (22) supports the racks (20) while the drying unit (32) performs at least partial extraction of at least one solvent from the applied mounting medium, and wherein the output drawer (22) has a retracted state in which the output drawer (22) is arranged inside the housing (26) and an extended state in which the output drawer (22) is arranged at least partly outside the housing (26) for removal of the coverslipped specimen slides (21) from the apparatus (10, 60, 70, 100, 110, 120).

9. The apparatus (10, 60, 70, 100, 110, 120) according to claim 8, wherein the output drawer (22) is manually movable between the retracted state and the extended state.

10. The apparatus (10, 60, 70, 100, 110, 120) according to claim 9, further comprising a drive unit (28), wherein the output drawer (22) is movable between the retracted state and the extended state both manually and by operation of the drive unit (28).

11. The apparatus (10, 60, 70, 100, 110, 120) according to claim 9, wherein the output drawer (22) includes a bottom element (42) having at least one opening (44);
wherein the drying unit (32) includes an air delivery unit (34) for delivering an air flow to the coverslipped specimen slides (21); and
wherein the air delivery unit (34) guides the air flow to the coverslipped specimen slides (21) through the at least one opening (44).

12. The apparatus (10, 60, 70, 100, 110, 120) according to claim 9, wherein the output drawer (22) includes two oppositely located side walls (102, 104), and at least one respective slit nozzle (80, 82) on at least one of the two oppositely located side walls (102, 104) for delivering an air flow to the coverslipped specimen slides (21).

13. The apparatus (10, 60, 70, 100, 110, 120) according to claim 8, further comprising a drive unit (28), wherein the output drawer (22) is movable between the retracted state and the extended state by operation of the drive unit (28).

14. The apparatus (10, 60, 70, 100, 110, 120) according to claim 13, wherein the output unit housing (72) includes a sliding door (76) for closing off the first opening (74).

15. The apparatus (10, 60, 70, 100, 110, 120) according to claim 13, wherein at least a sub-region of the housing (72) of the output unit (18) is insulated by an insulating medium.

16. The apparatus (10, 60, 70, 100, 110, 120) according to claim 8, wherein the output unit (18) includes a housing (72) having a first opening (74) through which the racks (20) are delivered to the output unit (18) and a second opening through which the output drawer (22) is displaceable, and wherein the output drawer (22) includes a front wall (24) that closes off the second opening when the output drawer (22) is in the retracted state.

17. The apparatus (10, 60, 70, 100, 110, 120) according to claim 16, wherein the air discharge unit (46) includes a filter for filtering discharged air.

18. The apparatus (10, 60, 70, 100, 110, 120) according to claim 16, wherein the drying unit (32) includes an air delivery unit (34) for delivering an air flow to the coverslipped specimen slides (21), wherein the air delivery unit (34) includes at least one air delivery conduit (36) for delivering the air flow, the air discharge unit (46) including at least one air discharge conduit (48) for discharging air; and
wherein the air discharge conduit (48) and the air delivery conduit (36) share at least one delimiting wall.

19. The apparatus (10, 60, 70, 100, 110, 120) according to claim 1, wherein the output unit (18) includes a housing (72) having a first opening (74) through which the racks (20) are delivered to the output unit (18) and a second opening through which the output drawer (22) is displaceable.

20. The apparatus (10, 60, 70, 100, 110, 120) according to claim 1, wherein the drying unit (32) includes an air discharge unit (46) for discharging solvent-containing air.

* * * * *